(12) United States Patent

Yamaguchi

(10) Patent No.: US 12,686,401 B2

(45) Date of Patent: Jul. 21, 2026

(54) SAFE DRIVING DETERMINATION APPARATUS

(71) Applicant: ISUZU MOTORS LIMITED, Tokyo (JP)

(72) Inventor: Kazuhiko Yamaguchi, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 709 days.

(21) Appl. No.: 17/908,897

(22) PCT Filed: Mar. 9, 2021

(86) PCT No.: PCT/JP2021/009368

§ 371 (c)(1),
(2) Date: Sep. 1, 2022

(87) PCT Pub. No.: WO2021/182484

PCT Pub. Date: Sep. 16, 2021

(65) Prior Publication Data

US 2024/0199046 A1 Jun. 20, 2024

(30) Foreign Application Priority Data

Mar. 11, 2020 (JP) ................................. 2020-042078

(51) Int. Cl.
B60W 50/00 (2006.01)
A61B 5/16 (2006.01)
(Continued)

(52) U.S. Cl.
CPC ............. B60W 50/14 (2013.01); A61B 5/168 (2013.01); A61B 5/18 (2013.01); G06V 20/58 (2022.01);
(Continued)

(58) Field of Classification Search
CPC ........... B60W 50/14; B60W 2540/225; B60W 2540/229; B60W 2050/143;
(Continued)

(56) References Cited

U.S. PATENT DOCUMENTS

2005/0280519 A1* 12/2005 Nagata ................... B60Q 9/008
340/438
2015/0166062 A1* 6/2015 Johnson ................. G08G 1/167
701/41
(Continued)

FOREIGN PATENT DOCUMENTS

CN 107685729 A 2/2018
CN 109969195 A 7/2019
(Continued)

OTHER PUBLICATIONS

JP2016207174A Translate (Year: 2016).*

*Primary Examiner* — Abby J Flynn
(74) *Attorney, Agent, or Firm* — PROCOPIO, CORY, HARGREAVES & SAVITCH LLP

(57) ABSTRACT

A safe driving determination apparatus includes an angle value calculation part that calculates an angle value indicating a face direction angle of a driver with respect to the traveling direction, a determination part that determines whether or not the driver is in a state of being inattentive to the road ahead on the basis of whether or not an integrated value of angle values during a past predetermined determination period is equal to or greater than a threshold value, and a road state identification part that identifies a state of a road on which the vehicle is traveling, wherein the determination part determines the determination period on the basis of the state of the road on which the vehicle is traveling.

2 Claims, 6 Drawing Sheets

(51) Int. Cl.

| | |
|---|---|
| *A61B 5/18* | (2006.01) |
| *B60W 50/14* | (2020.01) |
| *G06V 20/56* | (2022.01) |
| *G06V 20/58* | (2022.01) |
| *G06V 20/59* | (2022.01) |
| *G08B 6/00* | (2006.01) |

(52) U.S. Cl.
CPC .......... *G06V 20/588* (2022.01); *G06V 20/597* (2022.01); *G08B 6/00* (2013.01); *B60W 2050/143* (2013.01); *B60W 2050/146* (2013.01); *B60W 2540/225* (2020.02); *B60W 2540/229* (2020.02)

(58) Field of Classification Search
CPC ........... B60W 2050/146; B60W 40/06; G06V 20/58; G06V 20/597; G06V 20/588; A61B 5/168; A61B 5/18; G08B 6/00; G08G 1/167
See application file for complete search history.

(56) References Cited

U.S. PATENT DOCUMENTS

| | | | | |
|---|---|---|---|---|
| 2016/0250968 | A1* | 9/2016 | Shirakata | ............. B60K 28/066 |
| | | | | 340/576 |
| 2017/0001648 | A1 | 1/2017 | An et al. | |
| 2018/0037216 | A1 | 2/2018 | Otake | |
| 2018/0154905 | A1 | 6/2018 | Yoshizu | |
| 2019/0138790 | A1 | 5/2019 | Matsumura et al. | |
| 2020/0207363 | A1* | 7/2020 | Deshpande | ....... B60W 50/0098 |
| 2020/0282984 | A1* | 9/2020 | Mizoguchi | ......... B60W 60/005 |
| 2020/0327345 | A1* | 10/2020 | Schumacher | .......... G06V 20/58 |

FOREIGN PATENT DOCUMENTS

| | | |
|---|---|---|
| DE | 10 2017 117 244 A1 | 2/2018 |
| DE | 10 2018 127 886 A1 | 5/2019 |
| JP | 2016-207174 A | 12/2016 |
| JP | 2018-097398 A | 6/2018 |
| JP | 2019-087150 A | 6/2019 |
| JP | 2019-106164 A | 6/2019 |
| JP | 2020-024532 A | 2/2020 |

* cited by examiner

SAFE DRIVING DETERMINATION APPARATUS

CROSS-REFERENCE TO RELATED APPLICATIONS

The present application is a U.S. National Stage entry of PCT Application number PCT/JP2021/009368, filed on Mar. 9, 2021, which claims priority under 35 U.S.C § 119(a) to Japanese Patent Application No. 2020-042078, filed on Mar. 11, 2020, contents of which are incorporated herein by reference in their entirety.

TECHNICAL FIELD

The present disclosure relates to a safe driving determination apparatus.

BACKGROUND ART

Conventionally, an apparatus has been proposed that determines whether a driver is inattentive to the road ahead (looking aside) according to a face direction of a driver while driving a vehicle, and alerts the driver if the driver is determined to be inattentive to the road ahead. Patent document 1 discloses a device for determining a state of being inattentive with a function to determine whether or not a driver's line of sight faces a direction being inattentive to the road ahead.

PRIOR ART

Patent Document

Patent Document 1: Japanese Unexamined Patent Application Publication No. 2020-24532

SUMMARY OF INVENTION

Problems to be Solved by the Invention

The conventional device for determining a state of being inattentive determines that a driver is in a state of being inattentive to the road ahead if time during which a driver's line of sight faces a direction of being inattentive to the road ahead is longer than a predetermined amount of time. However, magnitude of an impact on the safety of a state of being inattentive to the road ahead varies depending on a state of a road. Therefore, if the device for determining a state of being inattentive determines whether or not a driver is in a state of being inattentive to the road ahead using the same criteria regardless of a state of a road, there is a problem that the device may determine the driver to be in the state of being inattentive to the road ahead and issue an alarm despite of a safe situation, or the device may determine the driver is not in the state of being inattentive to the road ahead and fail to issue the alarm despite of a dangerous situation.

The present disclosure focuses on this point, and an object thereof is to appropriately determine whether or not the driver is in a state of being inattentive to the road ahead regardless of a state of the road.

Means for Solving the Problems

A safe driving determination apparatus according to an embodiment of the present disclosure is a safe driving determination apparatus for acquiring an angle value indicating a face direction angle of a driver by using a traveling direction of a vehicle as a reference after capturing an image of the driver of the vehicle with an imaging device to determine whether or not the driver is in a state of being inattentive to the road ahead on the basis of the acquired angle value, the apparatus includes an angle value calculation part that calculates an angle value indicating a face direction angle of at least one of i) a face direction angle of the driver in a yaw direction with respect to the traveling direction or ii) a face direction angle of the driver in a pitch direction with respect to the traveling direction, a determination part that determines whether or not the driver is in a state of being inattentive to the road ahead on the basis of whether or not an integrated value of angle values during a past predetermined determination period is equal to or greater than a threshold value, and a road state identification part that identifies a state of a road on which the vehicle is traveling, wherein the determination part determines the determination period on the basis of the state of the road on which the vehicle is traveling.

The road state identification part may identify a width of a lane on which the vehicle is traveling as the state of the road, the determination part may set the determination period longer, if the width of the lane is equal to or greater than a threshold value, than the determination period in the case where the width of the lane is less than the threshold value.

The road state identification part may identify the width of the lane on which the vehicle is traveling as the state of the road, and the determination part may identify whether a road on which the vehicle is traveling is a highway or an ordinary road on the basis of the width of the lane, and sets the determination period longer, if the road is a highway, than the determination period in the case where the road is an ordinary road.

The road state identification part may identify a density of people or vehicles within a predetermined range from the vehicle on the road on which the vehicle is traveling as the state of the road, and the determination part may make the determination period shorter, if the density is equal to or greater than a threshold value, than the determination period in the case where the density is less than the threshold value.

The road state identification part i) may acquire, from an external device storing road state information that associates the time of day, a location of a road, and the density, the road state information corresponding to a time at which the vehicle is traveling, and ii) may identify, as the state of the road, the density associated with the position at which the vehicle is traveling in the acquired road state information.

The road state identification part may identify the width of the lane on which the vehicle is traveling and the density of people or vehicles within the predetermined range from the vehicle on the road on which the vehicle is traveling as the state of the road, and the determination part i) may set the determination period longer, if the width of the lane is less than a threshold value and the density is less than a threshold value, than the determination period set in the case where the density is equal to or greater than the threshold value, and ii) may set the determination period shorter, if the width of the lane is equal to or greater than the threshold value and the density is equal to or greater than the threshold value, than the determination period set in the case where the density is less than the threshold value.

The safe driving determination apparatus further includes an operation receiving part that receives, from the driver of the vehicle, a setting operation for setting a length of the determination period for each state of the road on which the vehicle is traveling, wherein the determination part may determine the determination period to be a length indicated by the setting operation received by the operation receiving part associated with the state of the road identified by the road state identification part.

Effect of the Invention

According to the present disclosure, it is possible to appropriately determine whether or not the driver is in a state of being inattentive to the road ahead regardless of a state of the road.

DESCRIPTION OF EMBODIMENTS

<Configuration of Vehicle S>

Figure 1:
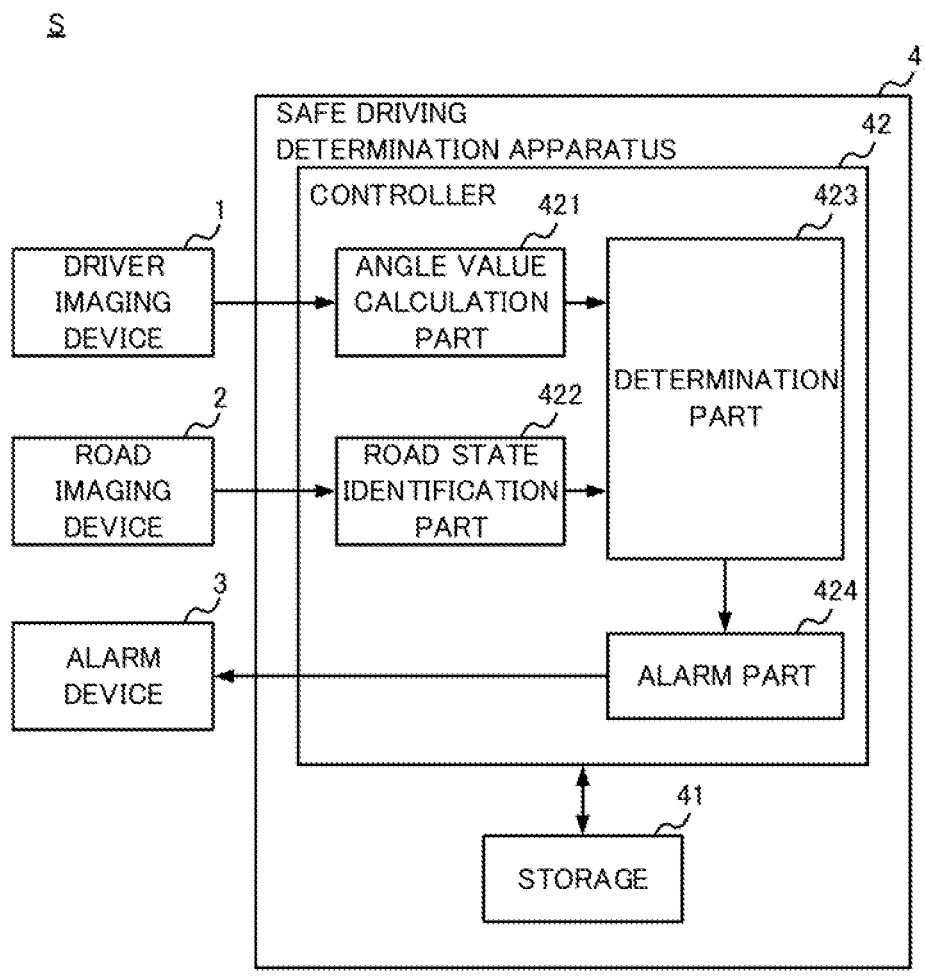
FIG. 1 shows a configuration of a vehicle S according to the present disclosure.

FIG. 1 shows a configuration of a vehicle S according to the present disclosure. The vehicle S includes a driver imaging device 1, a road imaging device 2, an alarm device 3, and a safe driving determination apparatus 4.

The driver imaging device 1 is provided to a driver's seat of the vehicle S, and includes a CCD camera, for example. The driver imaging device 1 captures an image of a driver sitting in the driver's seat from the front to generate a captured image. For example, the driver imaging device 1 captures an image of a driver's face while the vehicle S is traveling, and generates the captured image that enables identification of the driver's face direction angle with respect to the traveling direction of the vehicle S. The driver imaging device 1 outputs the generated captured image to the safe driving determination apparatus 4.

Figure 2A:
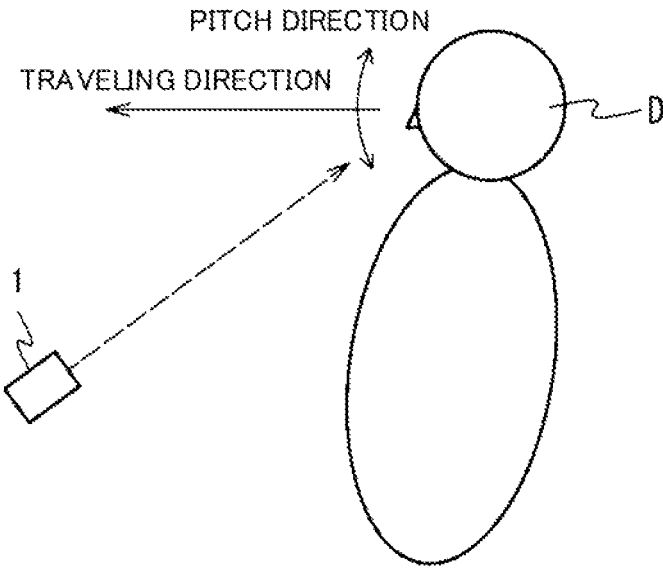
FIG. 2A shows a relationship between a driver imaging device 1 and a driver's face angle.
Figure 2B:
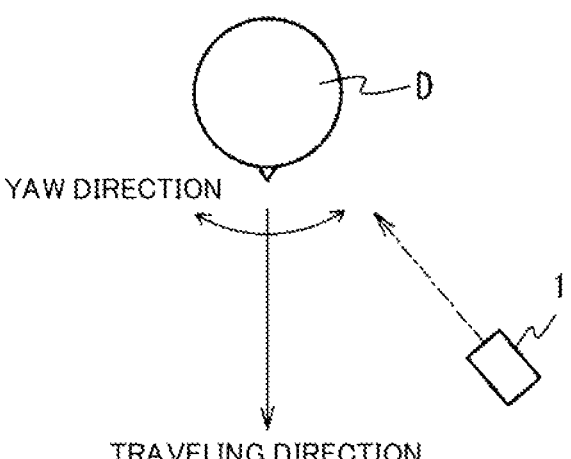
FIG. 2B shows a relationship between a driver imaging device 1 and a driver's face angle.

FIGS. 2A and 2B show a relationship between the driver imaging device 1 and a driver's face angle. FIG. 2A shows a side view of a driver D, and FIG. 2B shows a top view of the driver D. As shown in FIGS. 2A and 2B, the driver imaging device 1 is not in front of a driver D's face, but is provided diagonally downward from the driver D's face, for example.

The road imaging device 2 includes, for example, a plurality of CCD cameras, which capture images of the road in front of, behind, and to the left and right of a traveling vehicle S to generate captured images. For example, the road imaging device 2 captures an image of a lane or the like on which the vehicle S is traveling, and generates a captured image that enables identification of a width of the lane of the road on which the vehicle S is traveling. The road imaging device 2 outputs the generated captured image to the safe driving determination apparatus 4.

The alarm device 3 is a device that issues a warning to the driver on the basis of notification from the safe driving determination apparatus 4 that the driver is inattentive to the road ahead (for example, looking aside) while driving. The alarm device 3 includes a speaker for issuing an alarm, a display part for displaying a warning screen, and a vibration generation part for generating vibration, for example. It should be noted that the alarm device 3 may issue the alarm by combining at least two of sound, display, and vibration.

The safe driving determination apparatus 4 determines whether or not the driver is driving safely on the basis of a result of determining whether or not the driver is in a state of being inattentive to the road ahead. The safe driving determination apparatus 4 acquires an angle value indicating a face direction angle of the driver when the driver of the vehicle S is imaged by the driver imaging device 1 and the traveling direction of the vehicle S is used as a reference. The safe driving determination apparatus 4 identifies a state of the road, including the width of the lane in which the vehicle S is traveling, on the basis of the captured image captured by the road imaging device 2, for example.

The safe driving determination apparatus 4 determines whether or not the driver of the vehicle S is in the state of inattentive to the road ahead on the basis of the acquired angle value and the identified state of the road. If the safe driving determination apparatus 4 determines that the driver is in the state of being inattentive to the road ahead, the safe driving determination apparatus 4 notifies the alarm device 3 to issue the alarm.

The safe driving determination apparatus 4 includes a storage 41 and a controller 42. The storage 41 includes a storage medium such as a Read Only Memory (ROM), a Random Access Memory (RAM), and a hard disk. The storage 41 stores a program executed by the controller 42, which will be described later. The storage 41 stores information on the driver's face direction angle and the state of the road traveled by the vehicle S, for example.

The controller 42 is a Central Processing Unit (CPU), for example. The controller 42 functions as an angle value calculation part 421, a road state identification part 422, a determination part 423, and an alarm part 424 by executing the program stored in the storage 41. The controller 42 identifies the driver's face direction angle and the state of the road on which the vehicle S is traveling, and determines whether or not the driver is in the state of being inattentive to the road ahead.

The angle value calculation part 421 calculates the angle value of the driver's face direction on the basis of the captured image captured by the driver imaging device 1. The angle value calculation part 421 calculates the angle value indicating at least one of i) the driver's face direction angle in the yaw direction with respect to the traveling direction (FIG. 2B) or ii) the driver's face direction angle in the pitch direction with respect to the traveling direction (FIG. 2A). The angle value calculation part 421 notifies the determination part 423 about the calculated angle value.

The road state identification part 422 identifies the state of the road on which the vehicle S is traveling, on the basis of the captured image captured by the road imaging device 2. The state of the road includes the width of the lane on which the vehicle S is traveling, the type of the road, and the density of vehicles or people on the road, for example. The road state identification part 422 notifies the determination part 423 about the identified state of the road.

The road state identification part 422 identifies the number of vehicles different from the vehicle S, detected in front of, behind, and to the left and right of the vehicle S on the basis of the captured image acquired from the road imaging device 2, as the density of the vehicles on the road, for example. The road state identification part 422 identifies the number of people within a predetermined range (for example, within 10 meters) around the vehicle S as the density of people on the road, on the basis of the captured image acquired from the road imaging device 2, for example.

The determination part 423 determines whether or not the driver is in the state of being inattentive to the road ahead on the basis of whether or not the integrated value of angle values within a past predetermined determination period is equal to or greater than a threshold value. The determination part 423 determines a determination period on the basis of the state of the road on which the vehicle S is traveling identified by the road state identification part 422.

For example, if the width of the lane in which the vehicle S is traveling acquired from the road state identification part 422 is equal to or greater than the threshold value, the determination part 423 determines the determination period longer than that in the case where the width of the lane is less than the threshold value. The threshold value of the width of the lane is 3.5 meters, for example, which is the width of the lane that can distinguish a highway from an ordinary road.

Further, if the density of vehicles or people within the predetermined range (for example, within 10 meters) from the vehicle S obtained from the road state identification part 422 is equal to or greater than the threshold value, the determination part 423 may determine the determination period shorter than that in the case where the density of vehicles or people is less than the threshold value. The threshold value for the density of vehicles or people and the determination period determined by the determination part 423 are predetermined by experiment, for example, of levels with no safety problem.

If the determination part 423 determines that the driver of the vehicle S is in the state of being inattentive to the road ahead, the determination part 423 notifies the alarm part 424 that the driver is in the state of being inattentive to the road ahead. When the alarm part 424 receives a notification from the determination part 423 that the driver is in the state of being inattentive to the road ahead, the alarm part 424 notifies the alarm device 3 to issue the alarm.

<Operation of Determination Part 423>

Figure 3:
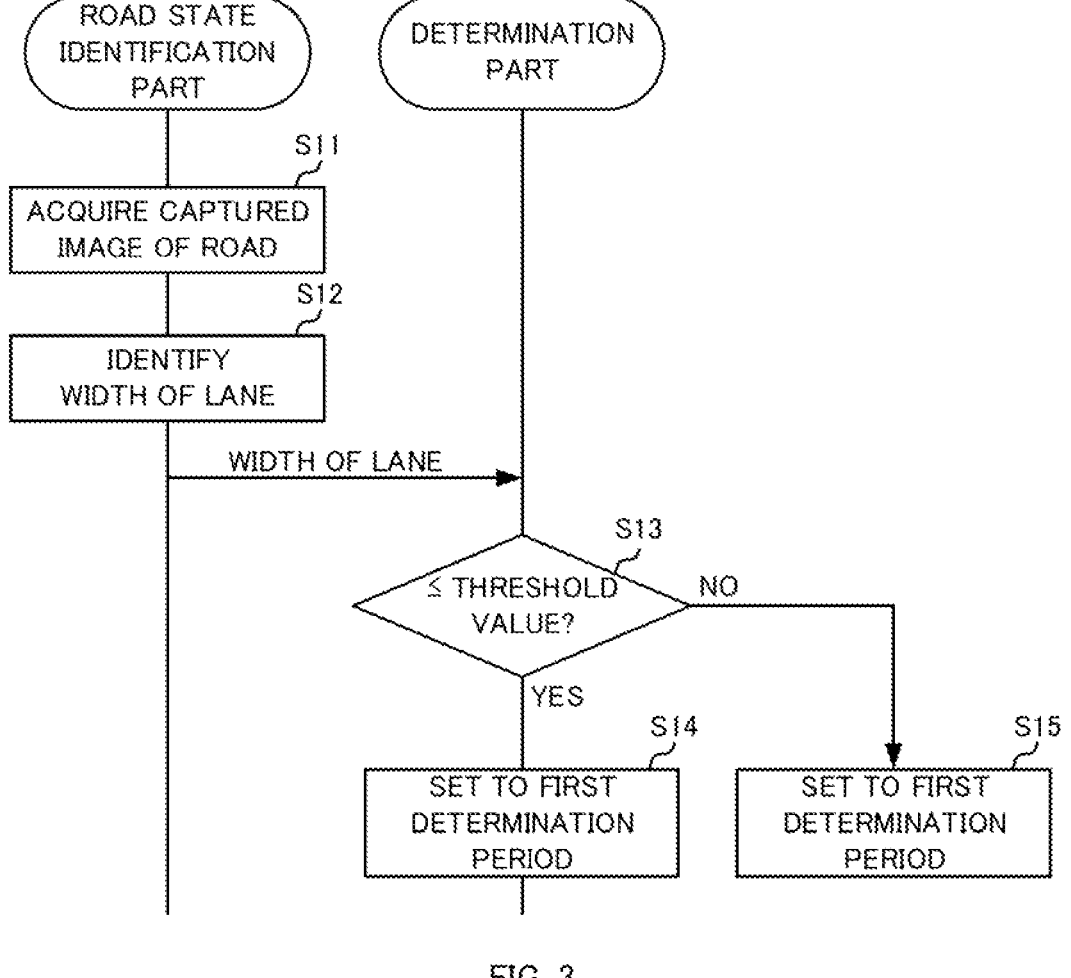
FIG. 3 is a flowchart of a process in which a determination part 423 sets a determination period on the basis of a width of a lane acquired from a road state identification part 422.

FIG. 3 is a flowchart of a process in which the determination part 423 sets the determination period on the basis of the width of the lane acquired from the road state identification part 422. The road state identification part 422 acquires the captured image of the road on which the vehicle S is traveling from the road imaging device 2 (step S11). The road state identification part 422 identifies the width of the lane in which the vehicle S is traveling as the state of the road on the basis of the acquired image of the road, and notifies the determination part 423 about the width of the lane (step S12). It should be noted that the road state identification part 422 may notify the determination part 423 about a numerical value indicating the width of the lane, or may notify the determination part 423 about information indicating the width of the lane (for example, "wide" or "narrow").

If the acquired width of the lane is equal to or greater than the threshold value (for example, 3.5 meters) (YES in step S13), the determination part 423 sets to a first determination period that is longer than the determination period in the case where the width of the lane is less than the threshold value (step S14). On the other hand, if the acquired width of the lane is less than the threshold value (NO in step S13), the determination part 423 sets to a second determination period that is shorter than the determination period in the case where the width of the lane is equal to or greater than the threshold value (step S15). The first determination period and the second determination period are predetermined by experiment, for example, as determination periods of levels with no safety problem.

By having the road state identification part 422 and the determination part 423 operate in this manner, the determination part 423 can set a longer determination period if the width of the lane is large. As a result, the safe driving determination apparatus 4 can restrict the alarm device 3 from issuing an erroneous alarm due to being too sensitive to a change in the angle of the driver's face direction in the case where, for example, the vehicle S is traveling on the highway with many straight roads and no people.

Figure 4:
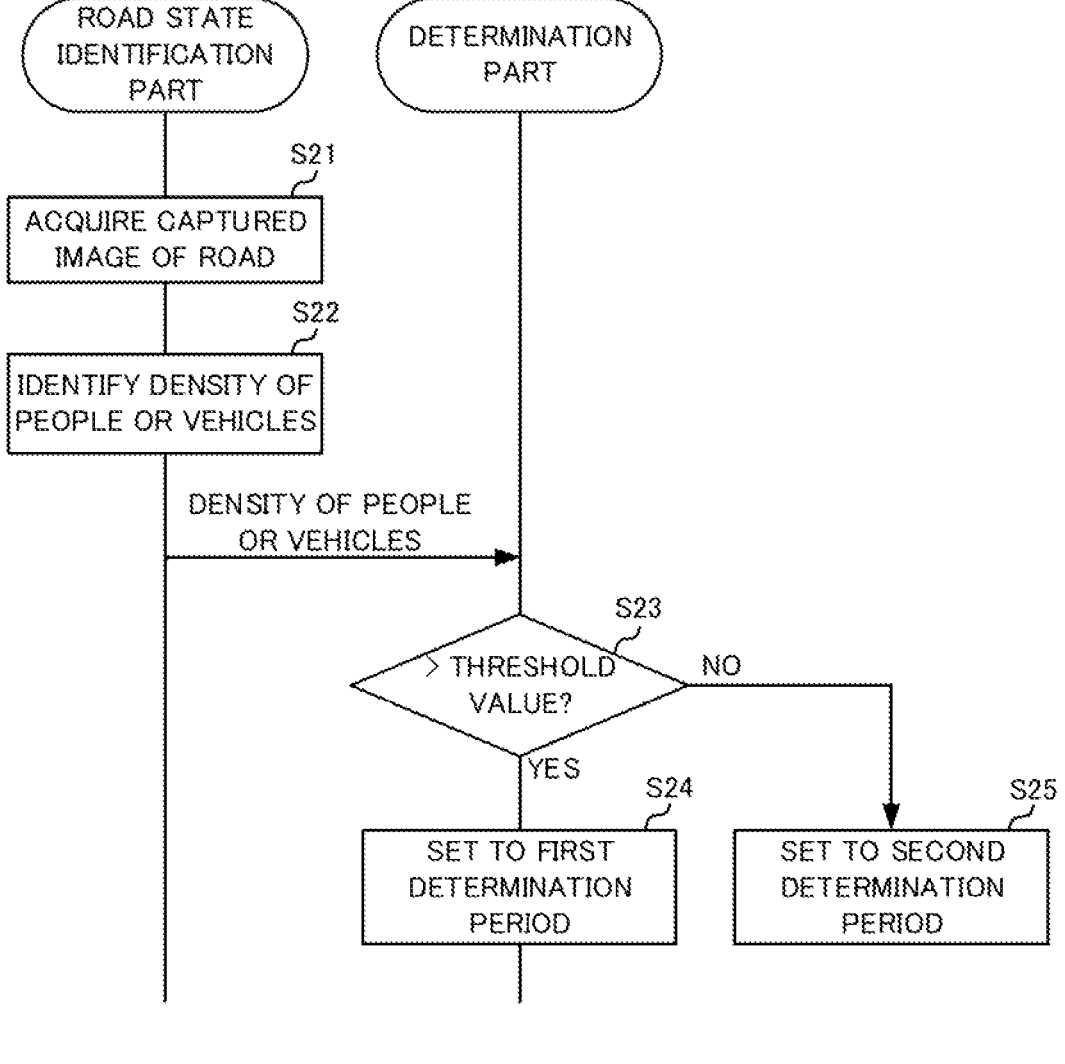
FIG. 4 is a flowchart of a process in which the determination part 423 sets the determination period on the basis of the density of people or vehicles acquired from the road state identification part 422.

FIG. 4 is a flowchart of a process in which the determination part 423 sets the determination period on the basis of the density of people or vehicles acquired from the road state identification part 422. The road state identification part 422 acquires the captured image of the road on which the vehicle S is traveling from the road imaging device 2 (step S21). The road state identification part 422 identifies, as the road state, the density of people or vehicles that are different from the vehicle S within a predetermined range from the vehicle S on the road on which the vehicle S is traveling, on the basis of the acquired image of the road, and notifies the determination part 423 about the density of people or vehicles (step S22).

The density of people within the predetermined range from the vehicle S identified by the road state identification part 422 is the number of people that can be detected within 10 meters from the vehicle S, for example. The density of vehicles within the predetermined range from the vehicle S identified by the road state identification part 422 is the number of vehicles detected in front of, behind, and to the left and right of vehicle S that are different from vehicle S, for example.

If the acquired density of people or vehicles is less than the threshold value (YES in step S23), the determination part 423 sets to the first determination period that is longer than the determination period in the case where the density of people or vehicles is equal to or greater than the threshold value (step S24). On the other hand, if the acquired density of people or vehicles is equal to or greater than the threshold value (NO in step S23), the determination part 423 sets to the second determination period that is shorter than the determination period in the case where the density of people or vehicles is less than the threshold value (step S25). The threshold value, the first determination period, and the second determination period have values predetermined by experiment, for example, of levels with no safety problem. The first determination period and the second determination period in FIG. 4 may be the same as or different from the first determination period and the second determination period in FIG. 3.

By having the road state identification part 422 and the determination part 423 operate in this manner, the determination part 423 can set shorter determination period if there are many vehicles or people around the vehicle S. As a result, the safe driving determination apparatus 4 can be sensitive to a change in the angle of the driver's face direction to make the alarm device 3 issue the alarm if, for example, the vehicle S is traveling on the ordinary road with many vehicles or people.

Further, the determination part 423 may combine both i) the determination based on the width of the lane on which the vehicle S shown in FIG. 3 is traveling and ii) the determination based on the density of vehicles or people in a predetermined range from the vehicle S shown in FIG. 4. For example, the determination part 423 may set the longer determination period even if the width of the lane on which the vehicle S is traveling acquired from the road state identification part 422 is less than the threshold value, if the density of vehicles or people within the predetermined range from the vehicle S acquired from the road state identification part 422 is less than the threshold value. On the other hand, the determination part 423 can set the shorter determination period if, for example, the width of the lane on which vehicle S is traveling obtained from the road state identification part 422 is equal to or greater than the threshold value, but the density of vehicles or people within the predetermined range from the vehicle S obtained from the road state identification part 422 is equal to or greater than the threshold value.

By having the determination part 423 operate in this manner, the safe driving determination apparatus 4 can restrict the alarm device 3 from issuing the alarm due to being too sensitive to a change in the driver's face direction in the case where the number of vehicles or people is small in the surroundings, for example, even if the width of the lane on which the vehicle S is traveling is small. On the other hand, the safe driving determination apparatus 4 can be sensitive to a change in the driver's face direction to make the alarm device 3 issue the alarm if there are many vehicles or people in the surroundings, for example, even if the width of the lane on which the vehicle S is traveling is large.

In the above-described operation, the determination part 423 may lengthen the determination period for determining whether or not the driver is in the state of being inattentive to the road ahead, if the vehicle S is traveling on the highway having many straight roads and no people, as compared with the case where the vehicle S is traveling on the ordinary road. As a result, the safe driving determination apparatus 4 can restrict the alarm device 3 from issuing the alarm due to being too sensitive to a change in the driver's face direction. On the other hand, for example, if the vehicle S is traveling on the ordinary road with many people, the determination part 423 shortens the determination period for determining whether or not the driver is in the state of being inattentive to the road ahead. As a result, the safe driving determination apparatus 4 can be sensitive to a change in the driver's face direction to make the alarm device 3 issue the alarm.

Figure 5:
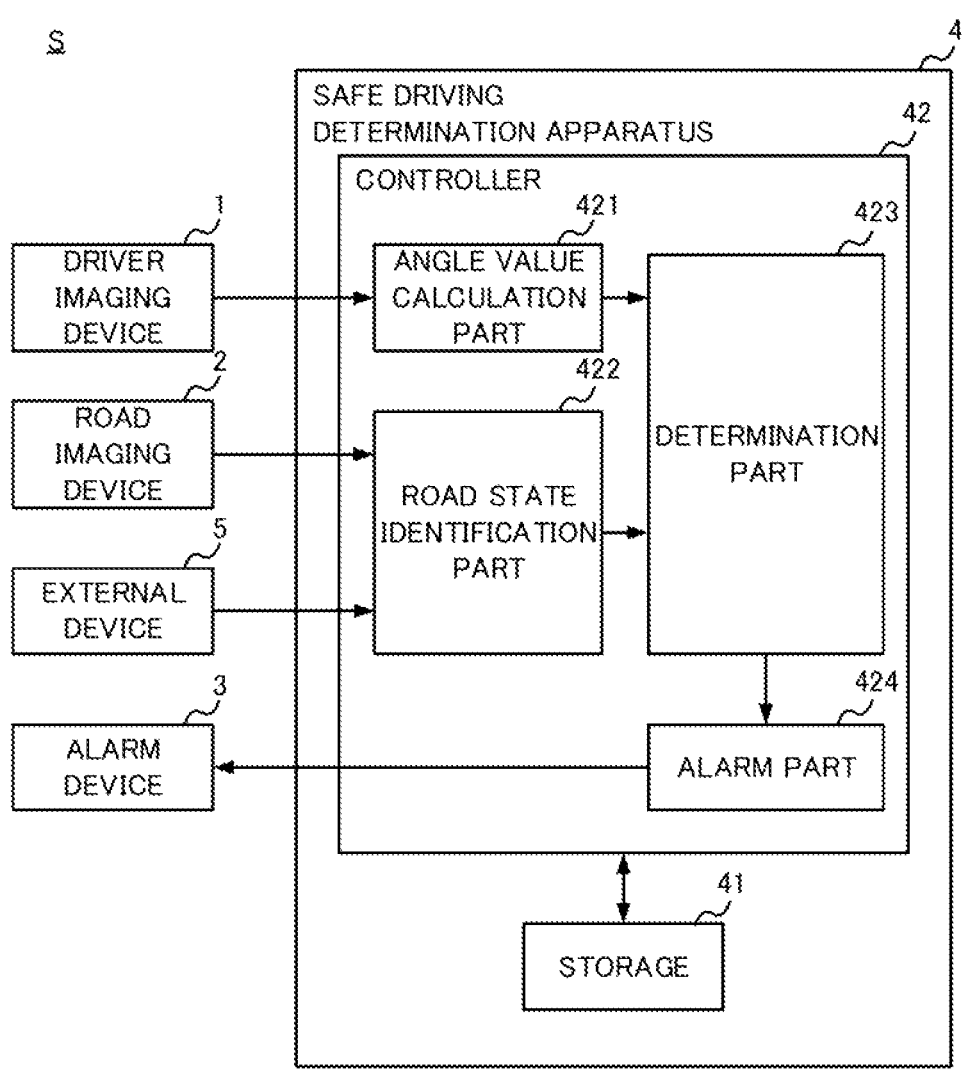
FIG. 5 shows the configuration of the vehicle S having an external device 5.

FIG. 5 shows the configuration of the vehicle S having an external device 5. The vehicle S is different from the vehicle S shown in FIG. 1 in that the vehicle S includes the external device 5, and is the same in other respects. The external device 5 is a car navigation system, for example. The external device 5 includes a position identification part that identifies a position at which the vehicle S is traveling.

The external device 5 stores road state information, which is associated with the time of day, the location of the road, and the density of vehicles or people within the predetermined range from the vehicle S. The road state identification part 422 notifies the external device 5 about the time when the vehicle S is in traveling. The external device 5 identifies, from the road state information stored in the external device 5, the density of vehicles or people within the predetermined range from the vehicle S, that is associated with i) the time when the vehicle S is traveling acquired from the road state identification part 422 and ii) position information identified by the position identification part included in the external device 5, and notifies the road state identification part 422 about the density. The road state identification part 422 notifies the determination part 423 about the density of vehicles or people within the predetermined range from the vehicle S, which is acquired from the external device 5.

By having the external device 5 and the road state identification part 422 operate in this manner, the determination part 423 can set the determination period on the basis of the road state information associated with the time and the position at which the vehicle S is traveling. Specifically, the determination part 423 can set the longer determination period at a time when there are fewer people on the road, such as early morning, and set the shorter determination period at a time when there are more people on the road, such as during the daytime, for example. As a result, the safe driving determination apparatus 4 can restrict the alarm device 3 from issuing the alarm due to being too sensitive to a change in the driver's face direction at a time such as early morning when there are few people on the road, for example. On the other hand, at the time of daytime when there are many people on the road, the safe driving determination apparatus 4 can be sensitive to a change in the driver's face direction to make the alarm device 3 to issue the alarm.

Figure 6:
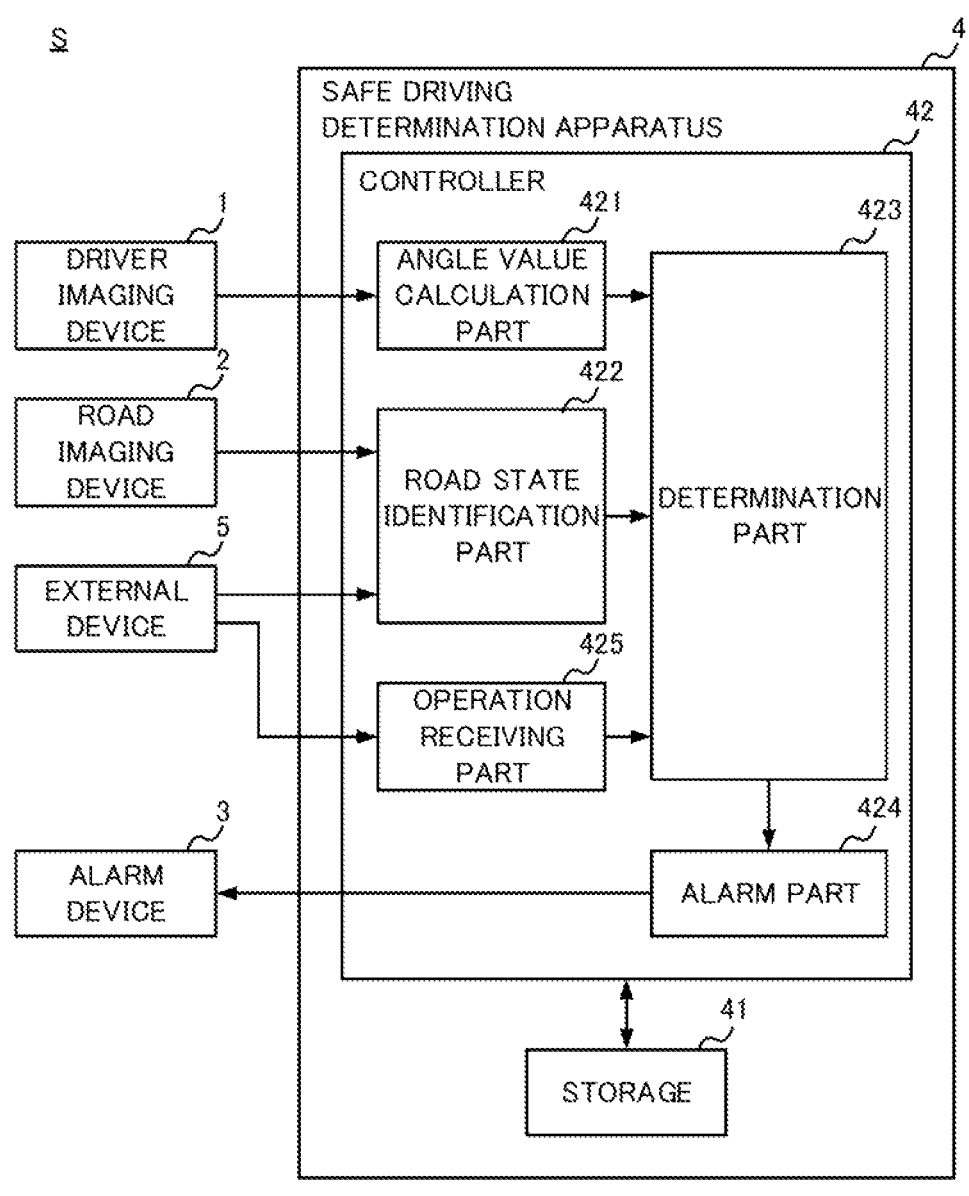
FIG. 6 shows the configuration of the vehicle S having an operation receiving part 425.

FIG. 6 shows the configuration of the vehicle S including an operation receiving part 425. The vehicle S differs from the vehicle S shown in FIG. 5 in that the vehicle S includes the operation receiving part 425, and is the same in other respects. The operation receiving part 425 receives a setting operation for setting the length of the determination period for each state of the road on which the vehicle S is traveling. The operation receiving part 425 receives the length of the determination period for each state of the road on which the vehicle S is traveling, which is set by the driver, for example, via an operation screen of the external device 5. The operation receiving part 25 notifies the determination part 423 about the received determination period.

The determination part 423 determines the determination period to be the length indicated by the setting operation received by the operation receiving part 425 associated with the road state identified by the road state identification part 422. By having the determination part 423 and the operation receiving part 425 operate in this manner, the determination part 423 can determine whether or not the driver is in the state of being inattentive to the road ahead on the basis of the driving condition of each driver. As a result, the safe driving determination apparatus 4 can respond to the driving condition of each driver, and can make the alarm device 3 issue the alarm on the basis of the state of the road on which the vehicle S is traveling.

<Effect of Safe Drive Determination Apparatus 4>

As described above, the controller 42 includes the angle value calculation part 421 that calculates the angle value of the driver of the vehicle S, the road state identification part 422 that identifies the state of the road such as the width of the lane on which the vehicle S is traveling, and the determination part 423 that determines whether or not the driver is in the state of being inattentive to the road ahead on the basis of the calculated angle value. The determination part 423 sets the determination period for determining whether or not the driver is in the state of being inattentive to the road ahead on the basis of the state of the road acquired from the road state identification part 422.

As a result, for example, if the width of the lane is small, the safe driving determination apparatus 4 is more sensitive to a change in the driver's face direction to make the alarm device 3 issue the alarm than when the width of the lane is large. Further, if the density of people or vehicles in the predetermined range from the vehicle S is high, the safe driving determination apparatus 4 is more sensitive to a change in the driver's face direction to make the alarm device 3 issue the alarm than when the density of people or vehicles is low. Therefore, the safe driving determination apparatus 4 can appropriately determine whether or not the driver is in the state of being inattentive to the road ahead regardless of the state of the road.

The present disclosure is explained on the basis of the exemplary embodiments. The technical scope of the present disclosure is not limited to the scope explained in the above embodiments and it is possible to make various changes and modifications within the scope of the disclosure. For example, all or part the apparatus can be configured with any unit which is functionally or physically dispersed or integrated. Further, new exemplary embodiments generated by arbitrary combinations of them are included in the exemplary embodiments of the present disclosure. Further, effects of the new exemplary embodiments brought by the combinations also have the effects of the original exemplary embodiments.

DESCRIPTION OF SYMBOLS

1 driver imaging device
2 road imaging device
3 alarm device
4 safe driving determination apparatus
5 external device
41 storage
42 controller
421 angle value calculation part
422 road state identification part
423 determination part
424 alarm part
425 operation receiving part
The invention claimed is:

1. A safe driving determination apparatus for acquiring an angle value indicating a face direction angle of a driver by using a traveling direction of a vehicle as a reference after capturing an image of the driver of the vehicle with an imaging device to determine whether or not the driver is in a state of being inattentive to a road ahead on a basis of the acquired angle value, the apparatus comprising:

a processor coupled to a memory storing instructions for the processor to execute:

an angle value calculation part that calculates an angle value indicating a face direction angle of at least one of i) a face direction angle of the driver in a yaw direction with respect to the traveling direction or ii) a face direction angle of the driver in a pitch direction with respect to the traveling direction, based on a captured image of the driver generated by the imaging device;

a determination part that determines whether or not the driver is in a state of being inattentive to the road ahead on the basis of whether or not an integrated value of angle values that the angle value calculation part calculates during a past predetermined determination period is equal to or greater than a threshold value;

a road state identification part that identifies a state of a road on which the vehicle is traveling, based on at least one of i) a captured image of a road generated by another imaging device different from the imaging device or ii) road state information which is acquired from an external device; and an alarm part that notifies an alarm device that includes a speaker for issuing an alarm, a display part for displaying a warning screen, and a vibration generation part for generating vibration, when the alarm part receives a notification that the driver is in the state of being inattentive to the road ahead from the determination part, such that the alarm device activates the speaker for issuing the alarm or the vibration generation part for generating the vibration, wherein the road state identification part:

i) acquires, from an external device storing road state information that associates a time of day, a location of a road, and a density of people or vehicles within a predetermined range from the vehicle on the road on which the vehicle is traveling as the state of the road, the road state information corresponding to a time at which the vehicle is traveling; and ii) identifies, as the state of the road, the density associated with a position at which the vehicle is traveling in the acquired road state information, and wherein the determination part makes a determination period shorter, if the density is equal to or greater than a threshold value, than the determination period in a case where the density is less than the threshold value.

2. A safe driving determination apparatus for acquiring an angle value indicating a face direction angle of a driver by using a traveling direction of a vehicle as a reference after capturing an image of the driver of the vehicle with an imaging device to determine whether or not the driver is in a state of being inattentive to a road ahead on a basis of the acquired angle value, the apparatus comprising:

a processor coupled to a memory storing instructions for the processor to execute:

an angle value calculation part that calculates an angle value indicating a face direction angle of at least one of i) a face direction angle of the driver in a yaw direction with respect to the traveling direction or ii) a face direction angle of the driver in a pitch direction with respect to the traveling direction, based on a captured image of the driver generated by the imaging device;

a determination part that determines whether or not the driver is in a state of being inattentive to the road ahead on the basis of whether or not an integrated value of angle values that the angle value calculation part calculates during a past predetermined determination period is equal to or greater than a threshold value;

a road state identification part that identifies a state of a road on which the vehicle is traveling, based on at least one of i) a captured image of a road generated by another imaging device different from the imaging device or ii) road state information which is acquired from an external device;

an operation receiving part that receives, from the driver of the vehicle, a setting operation for setting a length of a determination period for each state of the road includes a width of a lane on which the vehicle is traveling, a type of a road, and a density of vehicles or people on the road, which is set by the driver, via an operation screen of an external device; and an alarm part that notifies an alarm device that includes a speaker for issuing an alarm, a display part for displaying a warning screen, and a vibration generation part for generating vibration, when the alarm part receives a notification that the driver is in the state of being inattentive to the road ahead from the determination part, such that the alarm device activates the speaker for issuing the alarm or the vibration generation part for generating the vibration, wherein the determination part determines the determination period to be a length indicated by the setting operation received by the operation receiving part associated with the state of the road identified by the road state identification part associated with the state of the road identified by the road state identification part.

\* \* \* \* \*

12